United States Patent
Siney et al.

(10) Patent No.: US 11,517,422 B2
(45) Date of Patent: *Dec. 6, 2022

(54) INTRAOCULAR IMPLANTS COMPRISING DRUG-ELUTING MATERIALS WITH TIME RELEASE CHARACTERISTICS

(71) Applicant: VISUSNANO LIMITED, Hertfordshire (GB)

(72) Inventors: Elodie Jane Siney, Southampton (GB); Joanna Mary Gould, Rossett (GB); Darren Pitt, Herne Bay (GB); Philip Alexander, Eastleigh (GB)

(73) Assignee: VISUSNANO LIMITED, Hertfordshire (GB)

( * ) Notice: Subject to any disclaimer, the term of this patent is extended or adjusted under 35 U.S.C. 154(b) by 65 days.

This patent is subject to a terminal disclaimer.

(21) Appl. No.: 17/222,522

(22) Filed: Apr. 5, 2021

(65) Prior Publication Data
US 2021/0220117 A1    Jul. 22, 2021

Related U.S. Application Data

(63) Continuation of application No. 16/080,810, filed as application No. PCT/EP2017/054168 on Feb. 23, 2017, now Pat. No. 10,993,797.

(30) Foreign Application Priority Data

Feb. 29, 2016    (EP) ..................... 16157906

(51) Int. Cl.
*A61F 2/16*    (2006.01)
*A61F 9/00*    (2006.01)
(Continued)

(52) U.S. Cl.
CPC .............. *A61F 2/1613* (2013.01); *A61F 2/16* (2013.01); *A61F 9/0017* (2013.01); *A61L 27/18* (2013.01);
(Continued)

(58) Field of Classification Search
None
See application file for complete search history.

(56) References Cited

U.S. PATENT DOCUMENTS

| 5,652,059 A | 7/1997 | Margel |
| 2006/0035854 A1* | 2/2006 | Goldstein ............... A61L 31/16 424/45 |

(Continued)

FOREIGN PATENT DOCUMENTS

| CN | 101420991 | 4/2009 |
| CN | 103156708 A | 6/2013 |

(Continued)

OTHER PUBLICATIONS

English translation of CN 103156708 (referred to as Jiantao et al. in office actions) Publication Date of CN103156708: Jun. 19, 2013 (Jun. 19, 2013) (accompanied in this IDS with a certification of translation by Morningside IP).

(Continued)

*Primary Examiner* — Javier G Blanco
(74) *Attorney, Agent, or Firm* — Hoffman Warnick LLC; Franklin S. Abrams

(57) ABSTRACT

An intraocular lenses having a plurality of drug-containing microspheres attached to the intraocular lens. The intraocular lenses can be used for patients undergoing cataract surgery and reduces the need for recurrent surgery, follow-up treatment or postoperative eye-drops. Also provides a method for manufacturing such an intraocular lens and the use of an intraocular lens in the treatment of cataract.

18 Claims, 2 Drawing Sheets

(51) Int. Cl.
    *A61L 27/54*     (2006.01)
    *A61L 27/58*     (2006.01)
    *A61L 27/18*     (2006.01)
    *B29D 11/00*     (2006.01)

(52) U.S. Cl.
    CPC ............... *A61L 27/54* (2013.01); *A61L 27/58* (2013.01); *B29D 11/00096* (2013.01); *A61F 2002/1681* (2013.01); *A61F 2250/0067* (2013.01); *A61L 2300/604* (2013.01); *A61L 2300/622* (2013.01); *A61L 2300/624* (2013.01); *A61L 2300/626* (2013.01); *A61L 2430/16* (2013.01)

(56) References Cited

U.S. PATENT DOCUMENTS

| | | |
|---|---|---|
| 2006/0040894 A1 | 2/2006 | Hunter et al. |
| 2009/0130176 A1 | 5/2009 | Bossy-Nobs et al. |
| 2010/0016439 A1 | 1/2010 | Thomes et al. |
| 2010/0074942 A1 | 3/2010 | Ratner et al. |
| 2010/0226962 A1 | 9/2010 | Rodstrom et al. |
| 2012/0191185 A1 | 7/2012 | Colvin et al. |
| 2014/0073210 A1* | 3/2014 | Hartmann .............. D02G 3/404 428/323 |

FOREIGN PATENT DOCUMENTS

| | | |
|---|---|---|
| CN | 104434811 | 3/2015 |
| WO | WO 2007/041593 | 4/2007 |
| WO | WO/2009/075652 | 6/2009 |
| WO | WO 2012/021107 | 2/2012 |

OTHER PUBLICATIONS

Morningside IP certification of the English Language translation of CN 103156708 The Certificate of Translation is dated Nov. 17, 2020.
Chang et. al., "Intracameral dexamethasone reduces inflammation on the first postoperative day after cataract surgery in eyes with and without glaucoma," Clinical Ophthalmology, 2009, pp. 345-355.
Lawuyi et al., "The clinical utility of new combination phenylephrine/ketorolac injection in cararact surgery," Clinical Opthalmology, 2015, pp. 1249-1254.
"Achieving Excellence in Cataract Surgery: A Step-by-Step Approach," Ed. D. Michael Colvard, 2009, Chapter 12, pp. 95-108.
Zhu et al., "In-depth study on aminolysis of poly(e-caprolactone): Back to the fundamentals," Science China Chemistry, Nov. 2012, vol. 55, No. 11, pp. 2419-2427.
O'Donnel et al., "Preparation of microspheres by the solvent evaporation technique," Advanced Drug Delivery Reviews, 1997, vol. 28, pp. 25-42.
May 3, 2017 International Search Report issued in International Patent Application No. PCT/EP2017/054168.
May 3, 2017 Written Opinion of the International Searching Authority issued in International Patent Application No. PCT/EP2017/054168.
Dec. 9, 2020 European Search Report issued in European Patent Application No. 20193490.8.

\* cited by examiner

INTRAOCULAR IMPLANTS COMPRISING DRUG-ELUTING MATERIALS WITH TIME RELEASE CHARACTERISTICS

CROSS-REFERENCE TO RELATED APPLICATIONS

This application is a continuation of U.S. application Ser. No. 16/080,810, filed on Aug. 29, 2018, which is a U.S. National Stage of International Application No. PCT/EP2017/054168, filed on Feb. 23, 2017, published in English under PCT Article 21(2) as WO/2017/148791 on Sep. 8, 2017, which claimed priority to European Patent Application No. 16157906.5, filed on Feb. 29, 2016. The disclosures of the aforementioned European Patent Application No. 16157906.5, U.S. patent application Ser. No. 16/080,810, and International Application No. PCT/EP2017/054168 are hereby incorporated by reference in their entirety.

TECHNICAL FIELD OF THE INVENTION

The present invention provides intraocular lenses with drug-containing microspheres attached to the intraocular lens, preferably attached to one or more haptics of the intraocular lens. The microspheres may be configured to release a drug in a defined manner when the intraocular lens is inserted in an animal eye. Said intraocular lenses can thus be considered as intraocular lenses having controlled drug release, or drug-eluting intraocular lenses. Such intraocular lenses can be used for patients undergoing cataract surgery and reduces the need for recurrent surgery, follow-up treatment or postoperative administration of eye-drops.

Intraocular lenses (IOL) are lenses implanted in the eye used to treat cataracts or myopia.

The most common type of intraocular lens is the pseudophakic intraocular lens. These are implanted during cataract surgery, after the cloudy crystalline lens (otherwise known as a cataract) has been removed. The pseudophakic intraocular lenses replace the original crystalline lens, and provide the light focusing function originally undertaken by the crystalline lens.

The second type of intraocular lenses, more commonly known as a phakic intraocular lens (PIOL), is a lens which is placed over the existing natural lens, and is used in refractive surgery to change the eye's optical power as a treatment for myopia or nearsightedness.

Intraocular lenses usually consist of a small plastic lens with plastic side struts, called haptics, to hold the lens in place within the capsular bag inside the eye.

Insertion of an intraocular lens for the treatment of cataracts is the most commonly performed eye surgical procedure. Surgeons annually implant more than 6 million lenses. The procedure can be done under local anesthesia with the patient awake throughout the operation. The use of a flexible intraocular lens enables the lens to be rolled for insertion into the capsule through a very small incision, thus avoiding the need for stitches, and this procedure usually takes less than 30 minutes in the hands of an experienced ophthalmologist. The recovery period is about 2-3 weeks. After surgery, patients should avoid strenuous exercise or anything else that significantly increases blood pressure.

Cataract is defined as opacification of the lens within the eye and is the commonest cause of blindness worldwide. Cataract surgery is the commonest surgical procedure performed in the developed world. Despite advances in laser technology and micro-incision surgical platforms, cataract surgery still carries three main risks of: (1) postoperative intraocular inflammation, (2) infection, (3) secondary opacification of the lens capsule, known as posterior capsular opacification (PCO) and (4) glaucoma. If PCO develops, a further procedure, in the form of a laser is required.

Cataract extraction and implantation of an artificial intraocular lens (IOL) can restore patients' vision. After surgery, patients are required to administer eye drops, containing antibiotic and steroids, to reduce the risk of inflammation and infection. However, this requires good patient compliance, which may not be achievable in elderly patients with arthritis and other medical problems. Untreated intraocular inflammation leads to pain, redness, and retinal swelling, which can cause blurred vision. Post-operative infection, although rare, can result in catastrophic visual loss. The commonest complication after cataract surgery is posterior capsular opacification (PCO), which occurs in around 25% of patients. This is caused by proliferation of residual lens cells across the lens capsule, leading to a gradual deterioration in vision, and requires a further procedure for the successful treatment.

There are currently 300,000 lens replacement surgeries carried out by the NHS (National Health Service England) each year and another 100,000 in the private sector. Due to an ageing population, the rate of cataract surgery is increasing. There is currently a lot of interest in better and more effective treatments for cataracts.

PRIOR ART

Studies investigating whether a specific drug is useful for reduction of inflammation post cataract surgery are known. For example, one paper deals with the reduced inflammation on the first postoperative day after cataract surgery in eyes with and without glaucoma (cf. Diane T W Chang, "Intracameral dexamethasone reduces inflammation on the first postoperative day after cataract surgery in eye with and without glaucoma", in Clinical Ophthalmology, 2009:3, 345-355).

Directly coated drugs have the problem that drugs, such as cyclosporine A (CsA) are hydrophobic compounds with a large molecular weight and their permeability in eyes is poor. Therefore, its concentration in aqueous humor and other tissues is relatively low compared to the required therapeutic concentration, affecting its topical therapeutic effects. It has been shown that only 8% of CsA in eye drops reach corneal endothelium, only 1% reaches the anterior chamber, with the concentration in the posterior chamber, such as aqueous humor and vitreous far less than the required therapeutic level. Also, a huge percentage of drugs given through conventional administration lose their effects due tear drainage, absorption of nasopharyngeal mucosa and other factors.

One investigation studies the combination of phenylephrine/ketorolac injection as medication for use in cataract surgery (cf. L. El. Lawuyi, "The clinical utility of new combination phenylephrine/ketorolac injection in cataract surgery", in Clinical Opthalmology, 2015; 9, 1249-1254). The drawback of such a direct injection is the discomfort for the patient, as the injection has to be frequently renewed, as well as difficult control of the amount of injected drug.

Regarding intraocular lenses comprising releasable drugs, reference is made to CN 104434811 A, US 2009/130176 A, US 2010/016439 A, US 2012/191185 A, WO 12/021107 and US 2010/074942 A.

The present invention aims to solve the above-mentioned problems, i.e. aims at setting aside the complications occurring when common intraocular lenses are implanted, in particular for the treatment of cataract. Often, patients are required to administer eye drops after insertion of the intraocular lens on a regular basis, leading to decreased patient acceptance. If the patients do not administer the eye drops, or administer them on an irregular basis, this may lead to intraocular inflammation, pain, redness, and retinal swelling, which can cause blurred vision. On the other hand, when eye drops are administered directly onto the cornea or injected into the eye, this has to be done on a regular basis and the amount of drug actually reaching the target area can be hardly controlled. Also, the drugs may diffuse onto the pupilla, causing cloudy vision or visual impairment.

If as posterior capsular opacification develops, laser treatment is required. Laser treatment is a further procedure that is expensive for healthcare commissioners and requires an additional visit. Furthermore it has been associated with retinal detachment, damage to the lens optic, creation of floaters, and inducing retinal swelling (macula oedema). Therefore laser treatment should be avoided, if possible. Also, laser treatment can be hardly performed on animals, such as cats or dogs, as the procedure is commonly done under local anesthesia with the patient awake and upright throughout the procedure. However, animals, in particular cats or dogs, tend to move during such a procedure, and it is particularly difficult to achieve the fine focus required to achieve success with laser treatment in animals, such that the success of a laser treatment post-introduction of an IOL is very low and the risk to cause damage to the patient with the laser is very high.

In view of the above drawbacks and disadvantages, the present invention has been developed.

Short Description of the Invention

The present invention provides an intraocular lens, comprising a plurality of drug-containing microspheres attached to the intraocular lens. The intraocular lens may comprise an optic and at least one haptic. The microspheres can be attached to one or more haptics and/or the optic of the intraocular lens. The microspheres may be configured to release a drug in a defined manner when the intraocular lens is inserted in an animal eye. Animal in the context of the present application includes mammals, such as humans.

In a preferred embodiment, the intraocular lens includes a plurality of haptics, i.e. at least two haptics.

In a further preferred embodiment, the drug-containing microspheres are attached to each of the plurality of haptics. In a further preferred embodiment, the drug-containing microspheres are attached to each of the plurality of haptics as well as the optic.

A preferred way of attaching is done by covalently bonding the microspheres to the intraocular lens (e.g the haptics). The microspheres may be attached by using an acid or an amine group that forms an amide group. In this way, an amide bond can form between the amine group on the microspheres and the acid group on the intraocular lens, or between the acid group on the microspheres and the amine group on the intraocular lens.

In a further preferred embodiment, an optic of the intraocular lens is free of drug-containing microspheres. The microspheres may thus be attached only to the least one haptic of the intraocular lens, i.e. they may not be attached to the optic of the intraocular lens. In other words, in this embodiment, the optic will be free from attached microspheres.

At least some of the plurality of drug-containing microspheres may contain different drugs and/or may have different sizes.

The microspheres may have properties that allow controllably releasing or releasing in a defined manner a drug contained in the microspheres. Such an effect can be achieved by biodegradable microspheres, i.e. microspheres that are formed of a material comprising at least one biodegradable material such as a polymer. Particularly preferred materials that may be used according to the present invention are poly(L-lactic acid) and poly(lactic-co-glycolic acid), which are considered to have biodegradable properties.

The intraocular lens preferably may comprise at least one material selected from acrylates (such as polymethylmethacrylate (PMMA)), silicone (such as polydimethylsiloxane (PDMS)), hydrophobic acrylate, hydrophilic acrylate and collamer.

The one or more haptics may comprise at least one material selected from acrylates (such as poly(methyl methacrylate) (PMMA)), fluorinated polymers (such as polyvinylidene fluoride (PVDF)), polyimide (elastimide), and polyolefins (such as polypropylene (prolene)). In a preferred embodiment, the haptics may thus comprise at least one material selected from PMMA, PVDF, polyimide or polypropylene.

The optic and the one or more haptics of the intraocular lens may comprise the same or a different material.

The plurality of drug-containing microspheres may comprise or include microspheres containing at least one drug selected from antibiotics, anti-inflammatory, anti-hypertensive, anti-glaucoma and anti-proliferative agents. The microspheres may contain further materials such as solvents in which the drug are dissolved. Thus, the term drug-containing microspheres refers to microspheres at least containing drugs, but also containing other materials with which the drugs are commonly associated, in particular solvents.

The present invention also provides a method for manufacturing an intraocular lens according to the present invention, the method comprising steps of:
i) providing drug-containing microspheres;
ii) providing a precursor intraocular lens;
iii) activating the microspheres and/or the precursor intraocular lens; and
iv) attaching the microspheres to the precursor or activated intraocular lens. The microspheres may be attached to at least one or more haptics of the precursor or activated intraocular lens.

The providing the drug-containing microspheres may include preparing the microspheres by a solvent evaporation method.

The activating the microspheres may include applying an acid or a base to the microspheres. In a preferred embodiment one of an acid group, sodium hydroxide and a diamino linker may be applied to the microspheres.

The attaching the microspheres may include reacting one of an acid group and an amine group on the microspheres with one or more reactive groups on the precursor or activated intraocular lens.

The one or more haptics may have an open-loop design, a haptic angulation design or monobloc-plate style design.

The intraocular lens according to the present invention may particularly be used for the treatment of cataract. In a further preferred embodiment, the intraocular lens according to the present invention may be used for the treatment of glaucoma.

The intraocular lens can particularly be used in humans. The intraocular lens can also preferably be used in animals, in particular cats, dogs and horses.

The present invention also provides a method for cataract treatment, comprising: providing an intraocular lens including a plurality of drug-containing microspheres attached to the intraocular lens (e.g. attached to one or more haptics of the intraocular lens); inserting the intraocular lens into a capsular bag of an eye to be treated; and causing one or more drugs contained in the microspheres to be released into the eye. The present invention also provides a use of an intraocular lens according to the present invention for the treatment of cataract or glaucoma. The present invention also provides a method for the treatment of cataract or glaucoma, comprising the steps of: i) removal of the natural lens of the eye, and ii) inserting an intraocular lens according to the present invention into the eye.

DETAILED DESCRIPTION OF THE INVENTION

Figure 1:
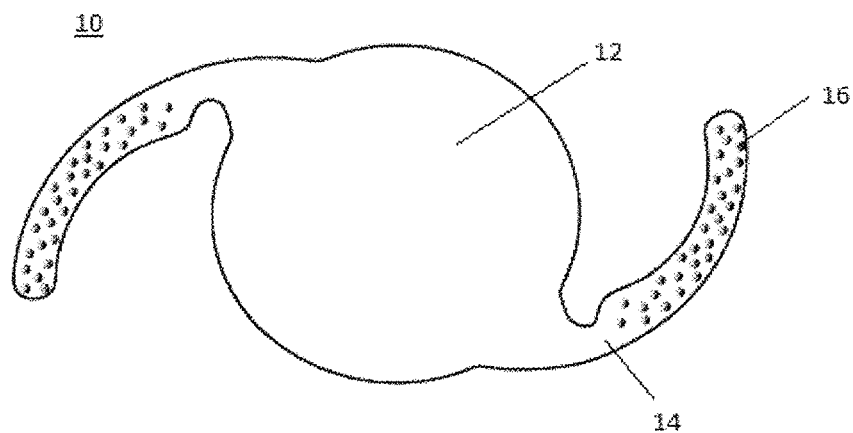
FIG. 1 shows a schematic illustration of an intraocular lens according to the present invention, wherein the microspheres are attached to the haptics of the intraocular lens.

The present invention solves the above problems by providing an intraocular lens (IOL), comprising a plurality of drug-containing microspheres attached to the intraocular lens. The intraocular lens may comprise an optic and at least one haptic. The microspheres can be attached to one or more haptics and/or the optic of the intraocular lens. In a preferred embodiment, the intraocular lens comprises at least two haptics. In the present invention, the term "microspheres" denotes drug-containing microspheres. The drug-containing microspheres may comprise at least a drug and a solvent.

In a preferred embodiment, the microspheres are configured to release a drug in a defined manner when the intraocular lens is inserted in an animal eye. The release of a drug in a defined manner may be understood as the controlled release of the drug over a prolonged period of time. The defined release bay thus be understood as controlling the release by external factors, such as the eye pH.

The intraocular lens may thus be provided with a plurality of microspheres attached to the one or more haptics and/or the optic, wherein the microspheres comprise at least one drug and are configured to release the at least one drug.

In a preferred embodiment, the intraocular lens includes a plurality of haptics, i.e. at least two, three or four haptics. In a particularly preferred embodiment, the intraocular lens includes two haptics. The haptics may be arranged on opposite sides of the optic of the intraocular lens. The one or more haptics may have an open-loop design, a haptic angulation design or monobloc-plate style design.

In a further preferred embodiment, the drug-containing microspheres are attached to each of the one or more haptics. In a preferred embodiment, an optic of the intraocular lens is free of drug-containing microspheres. The microspheres may thus be attached only to the least one haptic of the intraocular lens, i.e. they are not attached to the optic of the intraocular lens. In other words, in this embodiment, the optic will be free from attached microspheres.

In another preferred embodiment, at least some of the plurality of drug-containing microspheres contain different drugs and/or have different sizes.

It is noted that the term microspheres generally refers to spherial microparticles, but may also include microparticles not having a perfect spherical shape. Microspheres are small spherical particles, with diameters in the micrometer range (typically 1 µm to 1000 µm (1 mm)). Microspheres are sometimes referred to as microparticles. Microspheres can be manufactured from various natural and synthetic materials. Glass microspheres, polymer microspheres and ceramic microspheres are commercially available. Solid and hollow microspheres vary widely in density and, therefore, are used for different applications. Hollow microspheres are typically used as additives to lower the density of a material.

The microspheres may comprise at least one outer polymeric layer that forms the shape of the microsphere. The microspheres may be considered as generally hollow (even though substances such as a drug may be comprised) and may comprise at least one drug. In a preferred embodiment, the microspheres comprise at least a drug and a solvent. In the present invention, a microsphere may contain one drug or several different drugs. The intraocular lens may thus comprise a plurality of drug-containing microspheres, each containing more than one different drug. The intraocular lens may also have two or more different microspheres attached, wherein a first set of drug-containing microspheres contains one drug and a second set of drug-containing microspheres contains a different drug.

The microspheres may have different sizes. Microspheres defined by a specific size may exist in a size-range, i.e. the specific size provided may define an average size. The microspheres preferably have a size below 100 µm. The microspheres in the present invention may have a size in the range of 1-100 µm, more preferably of 1-50 µm, and even more preferably from 1-20 µm. In a preferred embodiment, the microspheres may have a size in the range of 2-100 µm, 10-100 µm-20-100 µm or 20-50 µm. The size of the microspheres may be measured by scanning electron microscope (SEM). SEM allows the easy measurement of microspheres attached to an intraocular lens.

When microspheres being <100 micrometer in diameter are used, this has the advantage that they fit into an injector syringe and into the lens capsule without causing unintentional drug release from the microspheres or cause the microspheres to become detached during insertion into the lens capsule.

The drug-containing microspheres may be configured to controllably release the at least one drug into an animal eye. The controlled release means that the drug is administered to the patient over a prolonged period of time, such as for at least one month. The release of drugs that can be detected in the UV-Vis region of the light spectrum can be measured by UV-Vis spectroscopy. Otherwise, biological assay or tagging of the drugs enables the detection thereof. Corresponding assays and measurement methods are known in the art. The measurement can also be done by determining the biological response, i.e. by measuring the intraocular inflammation of the eye, e.g. by assessing the anterior chamber cellular response and the anterior chamber "flare", which is caused by protein exudation. Alternatively, it is feasible to take samples of fluid from the front of the eye and measure the concentration of the samples.

In a preferred embodiment, the drug-containing microspheres are formed of biodegradable material. Biodegradability in the context of the present invention is regarded as the degradation within the eye in a period of 1 week to 12 months, preferably within 6 months, even more preferably within 4 months, depending on what drug has been encapsulated. Biodegradation in the eye is understood as the degradation of the microspheres in the eye medium. The microspheres may be seen as fully degraded when all of the contained drugs have been released.

The release may be controlled by adjusting the PLLA:PLGA ratio, the average molecular weight of the PLGA and PLGA polymers, the encapsulated drug, the size of the microspheres, the ratio of the glycolic acids to lactic acid monomers present in the PLGA, the PLGA/PLLA polymer end groups and the crystallinity.

An intraocular lens configured to release a drug in a defined manner or in a controlled manner enables that the patient or practitioner does not have to administer drugs manually, e.g. by way of eye drops or injection, post-insertion of the intraocular lens. In view of the intraocular lens being able to release drugs over an extended period of time, such as for at least 1 week, 2 weeks, 1 month, 2 months, 3 months, 4 months, 5 months, 6 months or 1 year, in particular for at least 2 to 6 weeks, 4 months or 6 months, there is no need for administering eye drops to the eye. Thus, the intraocular lenses are configured to release drugs for at least 1 week, 2 weeks, 1 month, 2 months, 3 months, 4 months, 5 months, 6 months, 1 year, in particular for at least 2 to 6 weeks, 4 months or 6 months. The skilled artisan will be able to define the required period of time based on the experience with the administration of eye drops to patients having undergone regular surgery with insertion of an intraocular lens. Thus, if, based on experience, eye drops are administered for 4 months to a patient, than the intraocular lens should be configured to release drugs for about 4 months.

Controlled release or release in a defined manner in the context of the present invention is understood as the delivery of compounds (such as drugs) in response to time. The timed release in the present invention is regarded as sustained release, i.e. release over a prolonged period of time. The defined release not only prolongs action, but it maintains drug levels within the therapeutic window to avoid potentially hazardous peaks in drug concentration following introduction of the intraocular lens and to maximize therapeutic efficiency.

Antibiotic release may be required for the first two weeks of the surgery, with a peak release at 2-5 days after surgery, as this is the time at which the infection is most likely to occur. Thus, an antibiotic drug may be released for at least 1 day to 1 month, 2 days to 1 month, 2 days to 2 weeks, 5 days to 2 weeks, or preferably 1 day to two weeks.

Anti-inflammatory drug release may be required for a duration of at least 1 week to 2 months, 1 week to 2 months or preferably for 4 to 6 weeks.

Anti-PCO drug release may be required for approximately 4-6 months, or possibly longer. Anti-PCO drugs may thus be released for 1 month to 1 year, 1 to 6 months, 2 to 6 months or preferably at least 4 to 6 months.

Anti-hypertensive drug release may be required for approximately 1 to 3 months, therefore anti-hypertensive drugs that are encapsulated into microspheres and attached to the IOL may be released for 2 weeks to 4 months.

The required drug concentrations differ depending on the drug. The drug concentrations can be provided as amount in mg per ml of solvent contained in the microspheres. The concentrations for the drugs may be:

For antibiotic drugs, such as intracameral antibiotic drugs (e.g. cefuroxime), the concentration in the drug-containing microspheres may be from 0.1 to 10 mg/0.1 ml, preferably from 0.2 to 5 mg/0.1 ml, even more preferably from 0.5 to 2.0 mg/0.1 ml, and even more preferably about 1.0 mg/0.1 ml.

For anti-inflammatory drugs, such as intracameral anti-inflammatory drugs (e.g. dexamethasone), the concentration in the drug-containing microspheres may be from 0.1 to 10 mg/0.1 ml, preferably from 0.2 to 5 mg/0.1 ml, even more preferably from 0.5 to 2.0 mg/0.1 ml, and even more preferably about 0.4 mg/0.1 ml. For the non-steroidal anti-inflammatory drugs (NSAID) (e.g. ketorolac), the concentration in the drug-containing microspheres may be up to 0.5 mg/0.1 ml.

For anti-PCO drugs, such as intraocular anti-PCO drugs (e.g. cyclosporine), the concentration in the drug-containing microspheres may be from 0.1 to 10 mg/0.1 ml, preferably from 0.2 to 5 mg/0.1 ml, even more preferably from 0.5 to 2.0 mg/0.1 ml, and even more preferably from 1.0 to 1.5 mg/0.1 ml. 0.3-0.5 g in total of anti-PCO drugs may be released over a 6 month period. As comparison, typical concentrations of eye-drops administered after surgery include: dexamethasone eye drops (0.1%) four times a day and cefuroxime 5% (i.e. 50 mg/ml) eye drops four times a day.

Higher doses than that usually used for eyedrops can be used, as the release of the drugs is controlled over a prolonged period of time.

The intraocular lenses commonly comprise a small plastic lens with plastic side struts or arms, called haptics, to hold the lens in place within the capsular bag inside the eye.

The optical portion of the lens, also usually simply called "optic" and also referred to as "lens portion" is usually a round biconvex structure which is usually slightly vaulted posteriorly.

The haptics are configured to stabilize the intraocular lens within the eye after insertion therein. The haptics can have an open-loop design, haptic angulation design, monobloc-plate style design or another special design. Typical designs for the haptics are disclosed in "Achieving Excellence in Cataract Surgery—A Step-by-Step Approach", Edited by D. M. Colvard, Chapter 12 "Intraocular lens materials and design", pages 95 to 108, 2009.

One particularly preferred shape of the haptics is the open-loop multipiece design. Open-loop intraocular lenses are held in place in the capsule bag by exerting a centripetal pressure on the capsule bag fornix and sometimes also the ciliary body, or in case of sulcus placement the ciliary sulcus. The haptics of an intraocular lens should maintain their original configuration during the implantation procedure. The haptic rigidity, which is the resistance of the haptic to forces that bend the loops centrally, and the haptic memory, which is the ability of the haptic to go back to its original configuration after having been bent, are the two factors that determine whether an intraocular lens will center well in an eye after implantation. Additionally, the contractive forces of the shrinking capsule bag due to fibrosis, especially in cases with zonule weakness or asymmetric shrinking, will need counteracting pressure from the haptics to ensure good centration.

Haptic materials that can be used in this invention are acrylates, fluorinated polymers, polyimides and polyolefins. Preferred materials are thus poly(methyl methacrylate) (PMMA), polyvinylidene fluoride (PVDF), polyimide (elastimide), and polypropylene (prolene). Particularly preferred are poly(methyl methacrylate) (PMMA) and polyimide.

The j-loop design results in pinpointed contact with the capsule bag equator, which may lead to stress folds of the posterior capsule, which usually disappear within the first months after surgery concomitant with the decrease in memory of the haptic material and this type of loop is the preferred type for intraocular lenses dedicated for sulcus placement.

The optic (lens portion) can be a flexible UV-blocking hydrophobic or hydrophilic acrylic with round or square edges, seamlessly joined to, or attached to, UV-blocking hydrophobic or hydrophilic acrylic haptic loops or haptic plate.

In the invention, the intraocular lens comprises microspheres that are attached to the intraocular lens (e.g. attached to at least one haptic of the intraocular lens). The microspheres contain at least one drug. The drug is contained in the inside of the microspheres and may be released in a defined manner over a prolonged period of time, e.g. as the microspheres are degraded.

The material of the microspheres can be any polymer that is biodegradable. Biodegradability in the context of the present invention is regarded as the degradation within the eye in a period of 1 week to 12 months, preferably within 6 months, even more preferably within 4 months.

Particularly preferred polymer materials according to the present invention are poly(L-lactic acid) (PLLA) and poly(lactic-co-glycolic acid) (PLGA) due to their biodegradability and biocompatibility. The microspheres of the present invention may comprise or be formed of a material comprising at least one polymer selected from poly(L-lactic acid) (PLEA) and poly(lactic-co-glycolic acid) (PLGA). It is noted that microspheres may in this particular case be defined in technical terms by the ratio of PLLA to PLGA. These biodegradable polymers have regulatory approval for human clinical use and have the advantage that their degradation can be tuned based on the ratio of different monomer units present. Depending on the drug and release rates required, the microspheres will comprise a mixture of poly(lactic-co-glycolic acid) (PLGA) and poly(L-lactic acid) (PLLA).

Figure 5:
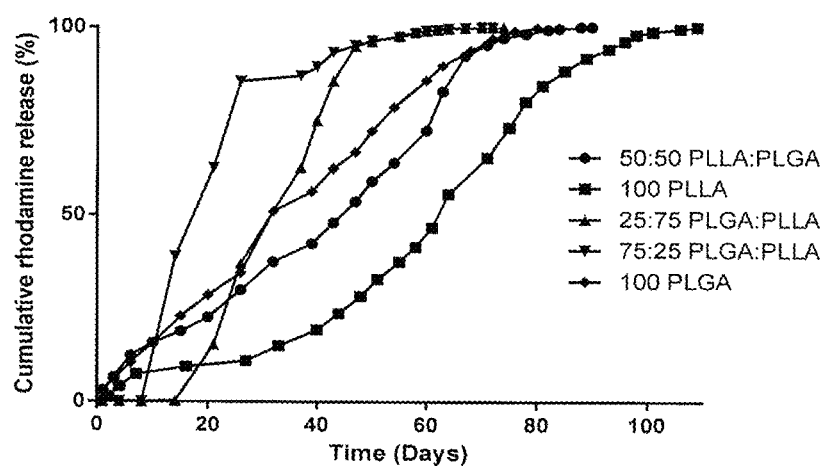
FIG. 5 shows an example of varying degradation times for microspheres, illustrating how the release times can be tuned using different ratios of the two polymers. Rhodamine B was encapsulated and release measured percentage of the total Rhodamine encapsulated.

FIG. 5 shows an example of varying degradation times for microspheres, illustrating how the release times can be tuned using different ratios of the two polymers. Rhodamine B was encapsulated and release measured percentage of the total Rhodamine encapsulated. The results were obtained by UV-Visible spectroscopy plotted against a calibration graph.

Biodegradability is commonly understood as the chemical dissolution of materials by bacteria, fungi, or other biological means. In the context of the present invention, biodegradability of the microspheres means that the microspheres will be degraded over a prolonged period of time in the eye medium.

The attachment to the intraocular lens will be defined further down below with respect to an embodiment in which the microspheres are attached to the haptics.

Types of drugs that may be used in the present invention and that are slowly and controllably released or released in a defined manner within the eye are antibiotics, anti-inflammatory agents, anti-hypertensive and anti-proliferative agents.

The microspheres contain physiologically relevant concentrations of drugs. The required drug concentrations differ depending on the drug. Typical concentrations may lie in the range of 0.1 to 10 mg/0.1 ml, preferably from 0.2 to 5 mg/0.1 ml, even more preferably from 0.5 to 2.0 mg/0.1 ml, and even more preferably about 0.5 to 1.0 mg/0.1 ml.

Typical solvents in which the drugs can be dissolved are known to the skilled person. Commonly, the solvents are identical to those used during the formation of the microspheres.

The drugs are released into the lens capsule over a period of up to at least 1 week, 2 weeks, 1 month, 2 months, 3 months, 4 months, 6 months or 1 year.

The invention thus provides a biodegradable polymer-based drug elution system (i.e. drug-containing microsphere) which can be attached to the intraocular lens, allowing slow and controlled release of antibiotics, anti-inflammatory, anti-proliferative or anti-hypertensive drugs within the eye.

Antibiotics may be selected from tacrolimus, sirolimus, everolimus, cyclosporine, and ascomycin, or mycophenolic acid.

Other drugs that may be included are cyclosporine to prevent PCO, carbonic anhydrase inhibitors or Apraclonidine as hypotensive agents, dexamethasone, a steroidal anti-inflammatory agent, ketorolac or nepafenac as non-steroidal inflammatory agents and the antibiotics cefuroxime and/or vancomycin.

Anti-PCO drug in the context of the present invention comprise drugs that are able to prevent PCO. The anti-PCO drugs may also have other additional properties, such an antibiotic or anti-inflammatory effect.

The microspheres may thus contain at least one of tacrolimus, sirolimus, everolimus, cyclosporine, ascomycin, mycophenolic acid, cyclosporine, dexamethasone, ketorolac or nepafenac, cefuroxime and/or vancomycin or a combination of any of these drugs.

The microspheres may be configured to release at least an antibiotic, an anti-inflammatory drug and an anti-PCO drug. In a preferred embodiment, the microspheres may contain all three types of drugs. In a further even more preferred embodiment, several microspheres, each containing a different type of drug may be used.

The microspheres of the present invention are attached to the intraocular lens. In a preferred embodiment, the microspheres are attached to haptics of the intraocular lens. In an even further preferred embodiment, the microspheres are only attached to the haptics of the intraocular lens. One such intraocular lens with microspheres only attached to the haptics is depicted in FIG. 1. In this Figure, an intraocular lens is generally designated 10 and includes a central optic 12 and a plurality of haptics 14 extending sideways (laterally) from the central optic 12. In the example case shown in FIG. 1, the plurality of haptics 14 are a pair. Among the pair, one haptic may serve as a leading haptic whereas the other haptic may serve as a trailing haptic. It is to be understood that the total number of haptics 14 is not limited to two in the present invention and that the intraocular lens 10 may comprise any number of haptics 14 larger or smaller than two as may be necessary and useful to accomplish the goal of a secure and reliable placement of the intraocular lens 10 within a capsular bag of an eye to be treated.

In the embodiment of FIG. 1, a plurality of drug-releasing microspheres 16 are attached to the intraocular lens 10 in the region of the pair of haptics 14, but not in the region of the central optic 12. In other embodiments, not all of the haptics 14 are provided with the drug-releasing microspheres 16. For example, one of the pair of haptics 14 of the intraocular lens 10 shown in FIG. 1 may be left free of the drug-releasing microspheres 16, so that all microspheres are provided in the region of the other of the pair.

When the microspheres are only attached to the haptics 14 of the intraocular lens and not the central portion or optic 12, this prevents and cloudy vision or visual impairment. Thus, compared to eye drops that diffuse into the eye or intraocular lenses that provide drugs over their whole surface, the attachment to the haptics only has the above-described advantage of no cloudy vision or visual impairment.

In a preferred embodiment, the microspheres are covalently bond to the intraocular lens. In a further preferred embodiment, the microspheres are attached via an acid or an amine group.

The attachment may be performed as described in the following. Once the drug has been encapsulated the surface of the microsphere can be reacted to allow for reaction onto the intraocular lens at a later stage. The microspheres may be activated first. Activation means that the microspheres are reacted and prepared for the attachment to the intraocular lens or haptics of the intraocular lens.

In one route, sodium hydroxide may be used to break the polymer structure of the microspheres to form an acid group which can be reacted further (Scheme 1A). In another route, a diamino linker may be used, which activates the surface to give a free amine which can be reacted further (Scheme 1B).

Scheme 1. Routes to activate the surface of the microspheres.

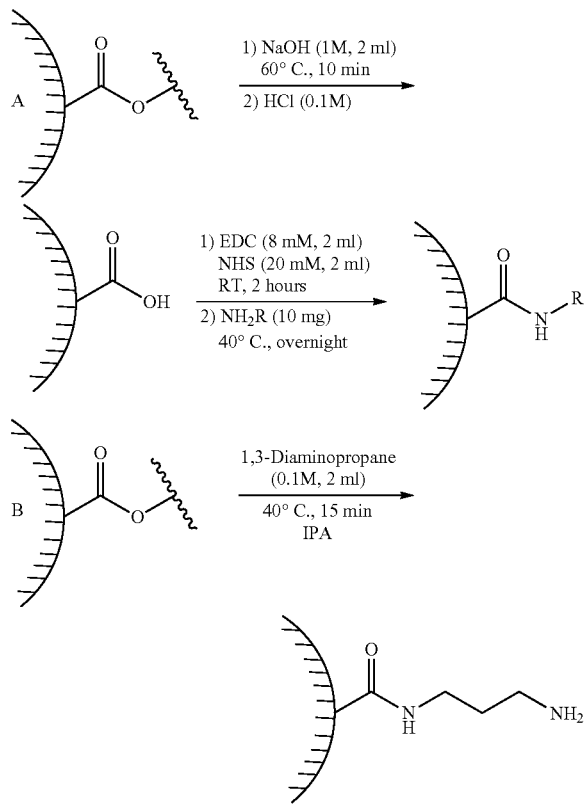

The first route enables to react onto any amine using "typical peptide coupling techniques". The second round enables to react onto ester, acyl chlorides, amides, anhydrides, carboxylic acids or alcohol groups present on the polymer.

Thus, the intraocular lens can firstly be broken down using acidic conditions and then the free acid chains on the intraocular lens can be coupled to the microspheres. Alternatively additional base can be added directly to the lens, which ensures that the primary group on the microsphere remains basic and can be reacted directly with the intraocular lens material. In the second route, the reactive group on the microspheres can be used to react with the intraocular lens. These lenses may comprise acrylic material, and are susceptible to hydrolysis due to the esters present. The intraocular lens can firstly be broken down using acidic conditions and then the free acid chains can be coupled to the microspheres using addition of base.

Reference is made to Y. Zhu et al, China Chem, 2012, 55, 2419-2427, which gives an example of activation by use of non-polar alcohols or small diamines to accelerate animolysis thereby creating primary —NH2 groups on a poly caprolactone (PCL) polymer.

In a preferred embodiment, the microspheres may thus be attached via a linker comprising an acid group or an amine group. The linker may thus comprise acid or amine groups and an alkyl chain.

In a further preferred embodiment of the present invention, the material of the intraocular lens is selected from polymethylmethacrylate (PMMA), silicone (e.g. PDMS), hydrophobic acrylate, hydrophilic acrylate and collamer. The optic, the one or more haptics and both the optic and haptics may be formed of these materials. Preferred materials are those that allow having a flexible intraocular lens, as this enables the lens to be rolled for insertion into the capsule through a very small incision, thus avoiding the need for stitches.

In a preferred embodiment, the intraocular lens is provided as a one-piece lens, i.e. where haptics and the optic are made from the same piece of material (e.g. acrylic). In another preferred embodiment, the intraocular lens is provided as a multi-piece lens, i.e. wherein the at least one haptic may be embedded into the body of the optic at the haptic-optic junction.

Polymethylmethacrylate (PMMA) has been used successfully in intraocular lenses. It has been shown that PMMA material did does show any rejection or foreign body reaction.

Silicone and acrylic are soft foldable inert materials. This allows the lens to be folded and inserted into the eye through a smaller incision. Specifically, acrylic lenses are a better choice in people who have a history of uveitis, or are likely to have to undergo retinal surgery requiring vitrectomy with replacement by silicone oil, such as persons with proliferative diabetic retinopathy or who are at high risk of retinal detachment, such as persons with high myopia. Thus, in a particularly preferred embodiment, the intraocular lens material is selected from silicon. In a further particularly preferred embodiment, the intraocular lens material is selected from acrylate.

One particular material for hydrophilic intraocular lenses is the trademarked "Natural Yellow". An intraocular lens material can incorporate the same UV-A blocking and violet light filtering chromophore that is present in the human crystalline lens. This material provides the exact chromophore the human retina naturally has for light protection.

Collamer is composed of collagen and copolymer material, is "bio-compatible" with the eye and contains up to 40% water.

In a preferred embodiment, the plurality of drug-containing microspheres include drug-containing microspheres containing at least one drug selected from antibiotics, anti-inflammatory agents, anti-hypertensive agents and anti-proliferative agents.

In a further preferred embodiment, the intraocular lens of the present invention is used for the treatment of cataract, i.e. as pseudophakic intraocular lens. It is noted that the intraocular lens can also be used as a lens which is placed over the existing natural lens, to change the eye's optical power as a treatment for myopia or nearsightedness, i.e. as phakic intraocular lens. The advantages of controlled release of drugs post-insertion can be beneficial for both kinds of intraocular lenses, i.e. for those used for the treatment of cataract and those for the correction of myopia. Nevertheless, in view of the many complications that may occur during the treatment of cataract, the intraocular lenses intraocular lens according to the present invention are particularly preferred for use in the treatment of cataract.

The intraocular lenses according to the present invention set aside the complications occurring when common intraocular lenses are implanted. One the one hand, patients are no longer required to administer eye drops after insertion of the intraocular lens on a regular basis, leading to increased patient acceptance. Also, there is no risk of forgetting to administer the eye drop, as the drugs are administered automatically in a defined manner over the required period of time. Thus, the risk of intraocular inflammation, pain, redness, and retinal swelling, which can cause blurred vision is considerably reduced.

When the microspheres are attached to the intraocular lens or the haptics of the intraocular lens, this prevents cloudy vision or visual impairment that may occur with common intraocular lenses or when eye drops are administered to the patient. Thus, the microspheres are preferably only attached to the at least one haptic and not to the optic.

If as posterior capsular opacification develops, laser treatment is required. This additional and annoying treatment can be prevented by using the intraocular lenses of the present invention. Following the intraocular insult from surgery, lens epithelial cells can proliferate along the haptic and optic or along the posterior capsule. As the haptic makes direct contact with the lens capsule, the drug-containing microspheres are in the ideal location to prevent this new cell growth. Therefore any drug that prevents cell proliferation, inhibits cell mitosis or promotes cell apoptosis in the local environment will prevent PCO and opacification of the optic. In the present invention an anti-PCO drug has the above-mentioned properties. The intraocular lenses of the present invention thus have the advantage that no PCO occurs, no laser treatment is required and thus will lead to higher patient comfort.

Also, laser treatment can be hardly performed on animals, such as cats or dogs, as the procedure is commonly done under local anesthesia with the patient awake throughout the operation. However, animals, in particular cats or dogs, tend to move, such that the success of a laser treatment post-introduction of an intraocular lens is very low. Thus, the intraocular lenses of the present invention, in view of their reduced risk of PCO, is beneficial for the treatment of animals, in particular cats and dogs.

The intraocular lens according to the present invention may thus preferably be used in the treatment of animals, in particular cats, dogs and horses.

The present invention also provides a method for manufacturing an intraocular lens, the method comprising the steps of:
i) providing drug-containing microspheres;
ii) providing a precursor intraocular lens;
iii) activating the microspheres and/or the precursor intraocular lens; and
iv) attaching the microspheres to the precursor or activated intraocular lens. The microspheres may be attached to at least one or more haptics of the precursor or activated intraocular lens.

Figure 2:
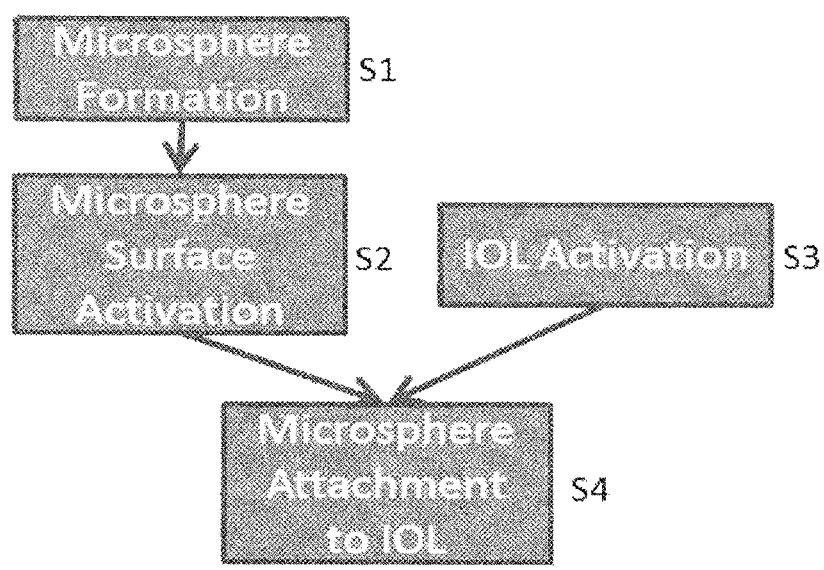
FIG. 2 is a schematic illustration of a method for manufacturing an intraocular lens with attached microspheres.

Such a method for preparing the intraocular lens comprising microspheres attached thereto is schematically shown in FIG. 2. Therein, the microspheres are formed (step S1) and surface activation is performed thereon (step S2). Separately, the precursor intraocular lens is activated (step S3). The precursor intraocular lens denotes a regular or conventional intraocular lens, e.g. one that may be commercially available. The precursor intraocular lens denotes an intraocular lens not having drug-containing microspheres attached thereto. Finally, both the activated microspheres are attached to the activated intraocular lens (step S4).

The microspheres can be prepared by any known method including solvent evaporation method, spray drying, dialysis and phase separation. In a preferred embodiment, the microspheres are formed by the solvent evaporation method. The solvent evaporation method can be easily optimized, resulting in excellent control over the diameter and shape of the microspheres formed.

A method for preparing microspheres using a solvent evaporation technique and LLA, PLLA and PLGA is described in "Adv Drug Deliv Rev. 1997 Oct. 13; 28(1):25-42. McGinity J W, O'Donnell PB." The solvent evaporation technique involves dissolving the polymers in a suitable immiscible solvent, the solution is then agitated in an aqueous solution resulting in emulsification. Microspheres are then formed from the hardening polymers as the solvent evaporates at the air/water interface. Difficulties with limited options for scale up, wide microsphere diameter distribution, and harsh physical burdens can diminish the activity of the drugs using these methods in comparison with the fairly mild solvent evaporation method.

In the solvent evaporation method, an emulsion is formed by dissolving a polymer into volatile organic solvent (also sometimes denoted as oil layer). This is then added to an aqueous layer with vigorous agitation to form an emulsion. As the volatile solvent evaporates, small microparticles are prepared. A component (such as, drug, dye or protein) can be encapsulated by addition thereof into the polymer oil mixture (polymer solvent mixture). One or more different drugs may be encapsulated by this method into the same microcapsule. Otherwise, several microcapsules, each containing a different drug may be prepared by performing the method several times with different drugs. In order to improve encapsulation, double emulsions can be prepared. Double emulsions are prepared by adding an initial emulsion into another phase. Most commonly to increase solubility of water soluble drugs, water/oil/water double emulsions are prepared. The first water in oil emulsion is prepared before being added into a larger water phase creating a water/oil/water double emulsion.

For example, a first polymer such as poly(vinyl alcohol) is added to deionized water. Biodegradable polymers, such as a mixture of PLLA:PLGA is dissolved in a solvent such as dichloromethane (DCM). The desired drug is then added into the biodegradable polymer in solvent solution and emulsified. The emulsified solution is added to the rapidly stirring first polymer solution and the mixture stirred to allow solvent evaporation. The solution is then transferred to a centrifuge tube and centrifuged. The first polymer solution is then decanted off and the microspheres washed in deionized water. The microspheres are isolated by filtration and dried in a vacuum desiccator.

The type and amount of drug can be adjusted according to the required treatment.

Figure 3:
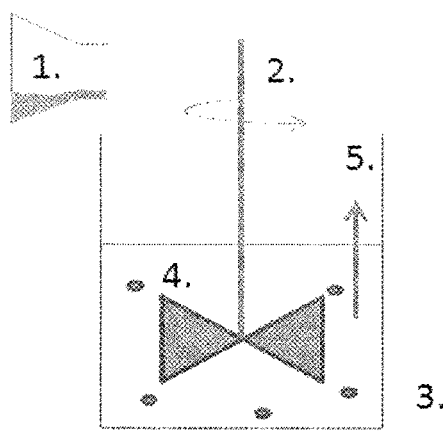
FIG. 3 shows a schematic illustration of preparation of microspheres by the solvent evaporation technique.

A typical setup for the preparation of microspheres by the solvent evaporation technique is depicted in FIG. 3: 1) The polymer is dissolved in an oil layer. 2) Agitation or mixing is required to split the oil droplets when in solution. 3) Water layer. 4) Oil/polymer droplets in solution. 5) Solvent evaporation occurs resulting in solid microspheres remaining.

Figure 4:
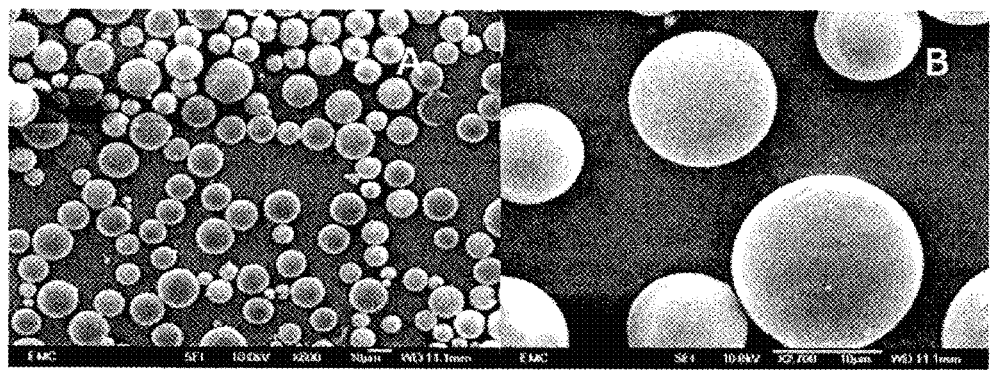
FIG. 4 show scanning electron micrographs of 50:50 PLLA:PLGA microspheres prepared using the solvent evaporation technique (A) Original magnification×600; (B) Original magnification×2700.

Scanning electron micrographs are shown in FIG. 4, of 50:50 PLLA:PLGA microspheres prepared using the solvent evaporation technique (A) Original magnification×600; (B) Original magnification×2700.

In a preferred embodiment, the method thus includes activating the microspheres including applying one of sodium hydroxide and a diamino linker to the microspheres.

In a further preferred embodiment, activating the microspheres includes applying one of sodium hydroxide and a diamino linker to the microspheres.

Once the drug has been encapsulated the surface of the microsphere can be reacted to allow for reaction onto the lens, such as an acrylic lens, at a later stage. For the microsphere activation, any route known in the art for activation of polymeric materials can be used.

A first preferred route that can be used in the present invention is to use sodium hydroxide to break the polymer structure of the microspheres to form an acid group which can be reacted further (cf. Scheme 1. A above).

A second preferred route that can be used in the present invention is to use a diamino linker, which activates the surface to give a free amine which can be reacted further (cf. Scheme 1. B above). This free amine group on the microspheres can be used to react with the intraocular lens, in particular an acrylic intraocular lens. These lenses are susceptible to hydrolysis due to the esters present. The intraocular lens can firstly be broken down using acidic conditions and then the free acid chains on the acrylic can be coupled to the microspheres using addition of base.

Thus, the activation of the microspheres may be performed by using sodium hydroxide or a diamino linker.

The activation of the intraocular lens and the attachment of the microspheres to the intraocular lens can be performed as follows.

This free amine group on the microspheres can be used to react with the acrylic intra ocular lens (IOL). These lenses are susceptible to hydrolysis due to the esters present. The intraocular lens can firstly be broken down using acidic conditions and then the free acid chains on the (acrylic) intraocular lens can be coupled to the microspheres. Alternatively additional base could be added directly to the lens, which would ensure that the primary amine on the microsphere remains basic and could be reacted directly with the acrylic.

In a preferred embodiment, the microspheres are thus attached by reacting at least an acid group or an amine group on the microspheres with reactive groups on the intraocular lens (such as ester or acid groups, which may have been used to cap the polymer chains of an acrylic).

In a preferred embodiment of the method, the microspheres are attached only to the haptics of the intraocular lens. In order to attach the microspheres only to the haptics, only the reactive groups in the haptic will be reacted with either the acid or base conditions to react with the reactive group on the microspheres. This may be done by e.g. physically keeping the optic outside the reaction conditions, i.e. not in the solvent with the drug-containing microspheres.

In a preferred embodiment, attaching the microspheres includes reacting one of an acid group and an amine group on the microspheres with one or more reactive groups on the precursor intraocular lens.

The intraocular lenses as described in this invention can be used for the treatment of diseases. The intraocular lenses with controlled release according to the present invention may in particular be used for the treatment of cataract.

The present invention also provides a method for cataract treatment or glaucoma, comprising: providing an intraocular lens including a plurality of drug-containing microspheres attached to the intraocular lens (e.g. one or more haptics of the intraocular lens); inserting the intraocular lens into a capsular bag of an eye to be treated; and causing one or more drugs contained in the microspheres to be released into the eye.

In the above description, it has been shown how intraocular lenses (IOLS) can be prepared that can release a drug in a defined manner. The intraocular lenses may thus have controlled release or drug eluting properties.

The invention provides a drug-containing microsphere which is attached to the intraocular lens, allowing controlled release of antibiotic, anti-inflammatory and anti-proliferative drugs within an animal eye over a prolonged period of time.

By attaching microspheres to the haptics of the intraocular lens, drugs contained in the microspheres can be controllably released to the site in the eye where they are required over a prolonged period of time.

In case the drug-containing microspheres are only attached to the one or more haptics of the intraocular lens, this assures that no cloudy vision or visual impairment is caused. As compared to eye drops, which are administered to the eye on a frequent basis and of which the administration can be hardly controlled, the device of the present invention allows providing a drug in a defined manner to only the region of the eye where it is required, without any drawbacks on the vision. Also, with eye drops, it is hard to control the concentration of drug administered. Similarly, injection of a drug is unpleasant for the patient and control of the concentration is hardly achieved.

This effect may in particular be preferable for the use after cataract surgery. The controlled drug release occurs through degradation of the microspheres that is tailored to the treatment course of each individual drug.

The intraocular lens according to the present invention reduces the risk of inflammation, infection and PCO. By improving patient outcomes, obviating the need for eye drops after surgery, and avoiding a second surgical procedure.

The intraocular lens according to the present invention also prevents post capsular opacification (PCO) and removes the need for eye drops following cataract surgery.

The intraocular lens having the controlled drug release confer an improvement, such as at least an 10-30% improvement in patient outcomes over standard care, therefore making it an attractive device for healthcare providers and results in tangible improvements for the patient.

The attachment of the microspheres to intraocular lenses therefore reduces the need for recurrent surgery, follow-up treatment or postoperative eye-drops.

This intraocular lens according to the present invention prevents new cell growth over the lens capsule and reduces the need for further treatment, benefiting patients and healthcare providers. The intraocular lens also incorporates antibiotic and anti-inflammatories (usually administered as eye drops post-surgery) to reduce problems associated with patient non-compliance.

The intraocular lens has the advantage that no treatment including topically administered eye drops is required, as the drug required post cataract surgery is included in the intraocular lens and administered over time.

The microspheres can be designed to encapsulate different drugs to treat different conditions and the drug release timings can be modified to suit need. The technique to prepare the microspheres may be the same for each drug. However, by altering the size, PLGA/PLLA ratio, the average molecular weight of the PLGA/PLLA in the microspheres, etc. the release may be tuned individually for each type of drug. In a preferred embodiment, only one drug may be encapsulated in the microspheres and a combination of different drug-containing microspheres may be attached to the at least one haptics.

EXPERIMENTAL RESULTS

Microsphere Preparation

The microspheres have been prepared using the conditions below:

Poly(vinyl alcohol) (0.05 g, RMM 31,000-50,000, Sigma-Aldrich) was added to deionized water (50 mL) and the mixture was rapidly stirred (2500 rpm). w:w ratios of PLLA (Resomer L 205, i.v. 0.8-1.2 dL g-1, 0.1% in chloroform, 25° C., RMM~100,000 obtained from Boehringer Ingelheim) and PLGA (Resomer RG 755 S, i.v. 0.5-0.7 dL g-1, 0.1% in chloroform, 25° C., RMM~20,000-80,000 obtained from Boehringer Ingelheim) having a total mass of 0.1 g were dissolved in dichloromethane (DCM) (4 mL). The drug (e.g. 1.25 µg, 0.05 mL) was then added in to the PLLA:PLGA in DCM solution and emulsified for 1 minute to 10 minutes. The PLLA:PLGA DCM solution was then added to the rapidly stirring PVA solution and the mixture was left to stir for 20 min to allow solvent evaporation. The solution was then transferred to a centrifuge tube and centrifuged for 4 min at 4000 rpm. The PVA solution was then decanted off and the microspheres were washed 3 times in deionized water. The microspheres were then isolated by filtration and dried in a vacuum desiccator.

Activation of Microspheres

Microspheres (0.15 g) were added to a premade solution (26 mL) of 1,3-diaminopropane (268 µL) in IPA (32 mL). The solution was heated at 40° C. in a sand bath for 15 min before being washed with water (6×40 mL) and dried under vacuum.

Microsphere Attachment

The Haptic of the intraocular lens was added to a weak HCl solution for 15 min before being washed with water. The activated microspheres were added in various ratios to the activated acrylic with 1 drop of triethylamine and reacted. These were then washed with DI water.

Test of Biodegradability of the Microspheres

The biodegradability was analyzed by SEM and indirectly by release of the drug. Once all the drug was released this was taken as indication that the microspheres had fully degraded.

Test of Release Rate of Microspheres Attached to an Intraocular Lens

Encapsulated microspheres attached to the intraocular lens were added into centrifuge tubes (Fisher Scientific) with phosphate buffered saline (PBS 0.01 M, 1 mL, pH 7.4, Sigma-Aldrich). The sealed tubes were kept at 37° C. and at set intervals the microspheres were centrifuged and the supernatant was collected for sampling after filtration through a 0.45 µm syringe filter (Fisher Scientific). The concentration of the drug was then determined measuring absorbance on a UV spectrometer against a calibration curve. Fresh PBS (1 mL) was added to the centrifuge tubes and placed back at 37° C.

The invention claimed is:

1. A composition comprising:
   a first material that is selected from an acrylate, a fluorinated polymer, a polyimide, a collamer, a silicone, or a polyolefin; and
   a second material that is a biodegradable polymer selected from the group consisting of poly(L- lactic acid) (PLLA), poly(lactic-co-glycolic acid) (PLGA) and combinations thereof, and comprises at least one encapsulated compound;
   wherein the first material is attached covalently via an acid group or an amine group to the second material, and wherein the encapsulated compound is a drug and is controllably released over a period of time;
   wherein the second material is surface activated by treatment with sodium hydroxide so as to provide a free acid group prior to covalent attachment to the first material, or surface activated by treatment with a diamino linker so as to provide a free amine group prior to covalent attachment to the first material; and
   wherein the composition is a component of a medical device.

2. The composition of claim 1, wherein the biodegradable polymer comprises a mixture of PLLA and PLGA.

3. The composition of claim 1, wherein the first material comprises an acrylate selected from the group consisting of a polymethylmethacrylate (PMMA), a hydrophobic acrylate and a hydrophilic acrylate.

4. The composition of claim 1, wherein the covalent attachment is via a peptide bond.

5. The composition of claim 1, wherein the first material is surface activated via treatment under acidic conditions prior to covalent attachment.

6. The composition of claim 1, wherein the covalent attachment comprises a linker.

7. The composition of claim 6, wherein the linker comprises an acid or an amino group.

8. The composition of claim 6, wherein the linker comprises an alkyl chain.

9. The composition of claim 1, wherein the first material is comprised within an intraocular lens.

10. An intraocular implant comprising:
    a first material that is selected from an acrylate, a fluorinated polymer, a polyimide, a collamer, a silicone, or a polyolefin; and
    a second material that is a biodegradable polymer selected from the group consisting of poly(L-lactic acid) (PLLA), poly(lactic-co-glycolic acid) (PLGA) and combinations thereof, and comprises at least one encapsulated drug compound;
    wherein the first material is attached covalently via an acid group or an amine group to the second material, and wherein the encapsulated drug compound is controllably released from the implant over a period of time after a surgical implantation;
    wherein the second material is surface activated by treatment with sodium hydroxide so as to provide a free acid group prior to covalent attachment to the first material, or surface activated by treatment with a diamino linker so as to provide a free amine group prior to covalent attachment to the first material.

11. The intraocular implant of claim 10, wherein the biodegradable polymer comprises a mixture of PLLA and PLGA.

12. The intraocular implant of claim 10, wherein the first material comprises an acrylate selected from the group consisting of a polymethylmethacrylate (PMMA), a hydrophobic acrylate and a hydrophilic acrylate.

13. The intraocular implant of claim 10, wherein the covalent attachment is via a peptide bond.

14. The intraocular implant of claim 10, wherein the implant is an intraocular lens.

15. The intraocular implant of claim 14, wherein the intraocular lens comprises one or more haptics.

16. The intraocular implant of claim 10, wherein the encapsulated drug compound is selected from an antibiotic, an anti-inflammatory, an anti-hypertensive, an anti-glaucoma, or an anti-proliferative agent.

17. The intraocular implant of claim 10, wherein the encapsulated drug compound is controllably released for at least one day after a surgical implantation.

18. The intraocular implant of claim 10, wherein the encapsulated drug compound is controllably released for at least one week after a surgical implantation.

\* \* \* \* \*